(12) United States Patent
Itoh et al.

(10) Patent No.: US 7,495,116 B2
(45) Date of Patent: Feb. 24, 2009

(54) PHOSPHOLIPID DERIVATIVE

(75) Inventors: Chika Itoh, Kanagawa (JP); Kazuhiro Kubo, Kanagawa (JP); Syunsuke Ohhashi, Kanagawa (JP); Tohru Yasukohchi, Kanagawa (JP); Hiroshi Kikuchi, Tokyo (JP); Norio Suzuki, Chiba (JP); Miho Takahashi, Fujieda (JP); Hitoshi Yamauchi, Tokyo (JP)

(73) Assignees: NOF Corporation, Tokyo (JP); Daiichi Pharmaceutical Co., Ltd., Tokyo (JP)

( * ) Notice: Subject to any disclaimer, the term of this patent is extended or adjusted under 35 U.S.C. 154(b) by 302 days.

(21) Appl. No.: 10/508,704

(22) PCT Filed: Mar. 28, 2003

(86) PCT No.: PCT/JP03/03966

§ 371 (c)(1),
(2), (4) Date: May 25, 2005

(87) PCT Pub. No.: WO03/082882

PCT Pub. Date: Oct. 9, 2003

(65) Prior Publication Data

US 2005/0220856 A1 Oct. 6, 2005

(30) Foreign Application Priority Data

Mar. 29, 2002 (JP) ............... 2002-093694

(51) Int. Cl.
*C07C 9/02* (2006.01)
(52) U.S. Cl. .................. 554/78; 424/450; 554/79; 554/82
(58) Field of Classification Search .......... 554/78, 554/79, 82; 424/450
See application file for complete search history.

(56) References Cited

U.S. PATENT DOCUMENTS

| | | | |
|---|---|---|---|
| 5,142,036 A | 8/1992 | Akimoto et al. | |
| 5,173,219 A | 12/1992 | Kim | |
| 5,395,619 A | 3/1995 | Zalipsky et al. | |
| 5,540,935 A | 7/1996 | Miyazaki et al. | |
| 5,631,018 A | 5/1997 | Zalipsky et al. | |
| 6,344,576 B1 | 2/2002 | Eibl | |
| 6,436,905 B1 | 8/2002 | Tonge et al. | |
| 2003/0144247 A1 | 7/2003 | Kuwano et al. | |
| 2006/0110436 A1 | 5/2006 | Ohhashi et al. | |
| 2006/0210618 A1 | 9/2006 | Kubo et al. | |
| 2007/0031481 A1 | 2/2007 | Itoh et al. | |

FOREIGN PATENT DOCUMENTS

| | | |
|---|---|---|
| EP | 0373621 | 6/1990 |
| EP | 0657463 | 6/1995 |
| EP | 1279406 | 1/2003 |
| JP | 63-221837 | 9/1988 |
| JP | 2-163108 | 6/1990 |
| JP | 6-228012 | 8/1994 |
| JP | 7-242680 | 9/1995 |
| JP | 7-268038 | 10/1995 |
| JP | 9-255740 | 9/1997 |
| JP | 2002-522442 | 7/2002 |
| WO | 99/09955 | 3/1999 |
| WO | 00/08031 | 2/2000 |
| WO | 00/33817 | 6/2000 |
| WO | 01/05375 | 1/2001 |
| WO | 01/74400 | 10/2001 |
| WO | 2004/029104 | 4/2004 |
| WO | 2004/060899 | 7/2004 |
| WO | 2004/083219 | 9/2004 |

OTHER PUBLICATIONS

H.M. Patel et al., Biochimica et Biophysica Acta, vol. 761, pp. 142-151, 1983.

(Continued)

*Primary Examiner*—Deborah D Carr
(74) *Attorney, Agent, or Firm*—Greenblum & Bernstein, P.L.C.

(57) ABSTRACT

A phospholipid derivative represented by the formula (1) (Z represents a residue of a compound having 3 to 10 hydroxyl groups; AO represents an oxyalkylene group having 2 to 4 carbon atoms; $R^1CO$ and $R^2CO$ represent an acyl group having 8 to 22 carbon atoms; X represents hydrogen atom, an alkali metal atom, ammonium or an organic ammonium; "a" represents an integer of 0 to 4; "b" represents 0 or 1; Q represents hydrogen atom or methyl group; m represents an average number of moles of the oxyalkylene group added; and m, k1, k2, and k3 are numbers satisfying the following conditions: $3 \leq m \leq 200$, $9 \leq m \times (k1+k2+k3) \leq 1000$, $1 \leq k1 \leq 2$, $0 \leq k2 \leq 9$ and $0 \leq k3 \leq 9$, and $3 \leq k1+k2+k3 \leq 10$), which is highly safe for living bodies, and is suitably used for solubilization and dispersion of physiologically active substances and the like, or in the fields of drug delivery systems such as liposomes and cosmetics.

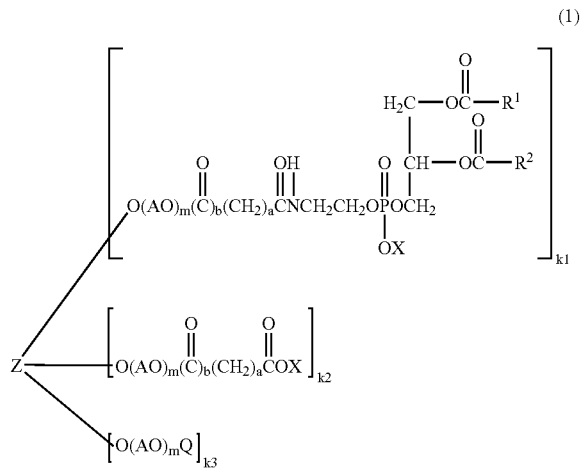

(1)

13 Claims, No Drawings

OTHER PUBLICATIONS

C.F. Gotfredsen et al., Biochemical Pharmacology, vol. 32, No. 22, pp. 3381-3387, 1983.
Pharmaceutical Society of Japan, 106th Annual Convention, Lecture Abstracts, pp. 336, 1986.
T.M. Allen et al., FEBS Letters, vol. 223, No. 1, pp. 42-46, Oct. 1987.
English Language Abstract of JP 63-221837, published Sep. 14, 1988.
A.L. Klibanov et al., FEBS Letters, vol. 268, No. 1, pp. 235-237.
S. Numi et al., Chemical and Pharmaceutical Bulletin, vol. 38, No. 6, pp. 1633-1638, 1990.
Y.S. Park et al., Biochimica et Biophysica Acta, vol. 1108, pp. 257-260, 1992.
English Language Abstract of JP 6-228012, published Aug. 16, 1994.
T. Yuda et al., Biological and Pharmaceutical Bulletin, vol. 19, No. 10, pp. 1347-1351, 1996.
R. Zeisig et al., Biochimica et Biophysica Acta, vol. 1285, No. 2, pp. 237-245, 1996.
T.M. Allen et al., Biochimica et Biophysica Acta, vol. 1061, No. 1, pp. 56-64, 1991.
English language abstract of JP 7-242680, published Sep. 19, 1995.
English language abstract of JP 2-163108, published Jun. 22, 1990.
English language abstract of JP 9-255740, published Sep. 30, 1997.
English language abstract of JP 2002-522442, published Jul. 23, 2002.
Database WPI, Section Ch, Week 199546, Derwent Publications Ltd., London, GB, AN 1995-355265, XP002354282; accompanied by family member JP 07-242680 A.
English language abstract of JP 7-268038, published Oct. 17, 1995.

PHOSPHOLIPID DERIVATIVE

TECHNICAL FIELD

The present invention relates to a phospholipid derivative containing a multi-arm polyalkylene oxide and a method for producing the same. The present invention also relates to a surfactant, solubilizer, dispersing agent for cosmetics, and lipid membrane structure containing the phospholipid derivative.

BACKGROUND ART

It is known that microparticle drug carriers including liposome formulations as a typical example and polypeptides of protein preparations and the like have poor retention in blood after intravenous administration and are readily captured by the reticuloendothelial system (henceforth abbreviated as "RES") of liver, spleen and the like. The presence of RES is a serious obstacle when preparations are utilized such as targeting type preparations which can deriver medicaments to organs other than RES, or microparticle drug carriers as sustained release type preparations which can provide long term blood retention of medicaments and achieve control release of the medicaments.

Researches have been conducted so far to impart microcirculatability to the aforementioned preparations. For example, from a standpoint that physicochemical properties of lipid bimolecular membranes of liposomes are relatively easily controllable, some methods have been proposed such as a method of increasing blood level of liposomes by using a smaller size of liposomes (Biochimica et Biophysica Acta, vol. 761, p. 142, 1983), a method of using lecithin having a high phase transition temperature (Biochemical Pharmacology, vol. 32, p. 3381, 1983), a method of using sphingomyelin instead of lecithin (Biochemical Pharmacology, vol. 32 volumes, p. 3381, 1983), and a method of adding cholesterol as a membrane component of liposomes (Biochimica et Biophysica Acta, vol. 761, p. 142, 1983). However, among the aforementioned methods, no method is known to successfully provide microparticle drug carrier which has excellent retention in blood and is hardly taken up by RES.

As other solutions, researches have been conducted for imparting microcirculatability and avoiding RES by membrane surfaces modification of liposomes with glycolipids, glycoproteins, amino acid lipids, polyethylene glycol lipids or the like. For example, those reported as substances for such modification include glycophorin (Pharmaceutical Society of Japan, 106th Annual Convention, Lecture Abstracts, p. 336, 1986), ganglioside GM1 (FEBS letter, vol. 223, p. 42, 1987), phosphatidylinositol (FEBS Letter, vol. 223, p. 42, 1987), glycophorin and ganglioside GM3 (Japanese Patent Unexamined Publication (Kokai) No. 63-221837), polyethylene glycol derivative (FEBS Letter, vol. 268, p. 235, 1990), glucuronic acid derivative (Chemical and Pharmaceutical Bulletin, vol. 38, p. 1633, 1990), glutamic acid derivative (Biochimica et Biophysica Acta, vol. 1108, p. 257, 1992), polyglycerin phospholipid derivative (Japanese Patent Unexamined Publication No. 6-228012) and the like.

As for the modification of polypeptide, introduction of two water-soluble polymer molecules by using triazine and other methods have been reported in order to reduce binding sites of a polypeptide and thereby increase an amount of remaining active groups such as lysine residues in the polypeptide. Also as for liposome preparations, a method is reported in which two water-soluble polymer molecules are introduced into triazine to increase molecular weight of the water-soluble polymers, and liposome surfaces are modified by using the polymers. The number of the water-soluble polymers in said modification is limited up to 2. It is considered that, in this attempt, an effect of imparting microcirculatability to liposome surfaces is lower than liposomes with the hydrophilic groups. Furthermore, although phospholipid derivatives containing a polyalkylene oxide group have been used also as surfactants, no derivative has been known which is highly safe for living bodies and stably usable under a high salt concentration condition.

DISCLOSURE OF THE INVENTION

An object of the present invention is to provide a novel phospholipid derivative containing a polyalkylene oxide. More specifically, the object of the present invention is to provide a phospholipid derivative which is highly safe for living bodies, and is suitably used for solubilization and dispersion of physiologically active substances and the like, or in the fields of drug delivery systems such as liposomes and cosmetics. The inventors of the present invention conducted various studies to achieve the foregoing object. As a result, the inventors successfully provided novel phospholipid derivatives represented by the following formula and a method for producing the same.

The present invention thus provides a phospholipid derivative represented by the following general formula (1):

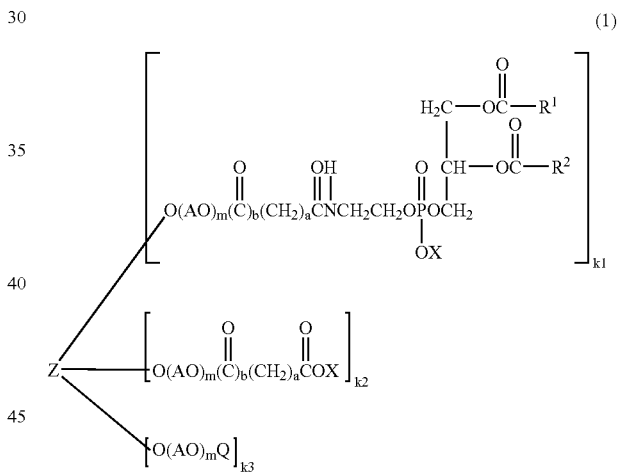

wherein Z represents a residue of a compound having 3 to 10 hydroxyl groups; AO represents an oxyalkylene group having from 2 to 4 carbon atoms; $R^1CO$ and $R^2CO$ independently represent an acyl group having 8 to 22 carbon atoms; X represents hydrogen atom, an alkali metal atom, ammonium or an organic ammonium; "a" represents an integer of 0 to 4; "b" represents 0 or 1; Q represents hydrogen atom or methyl group; m represents an average number of moles of the oxyalkylene group added; and m, k1, k2, and k3 are numbers satisfying the following conditions: $3 \leq m \leq 200$, $9 \leq m \times (k1+k2+k3) \leq 1000$, $1 \leq k1 \leq 2$, $0 \leq k2 \leq 9$ and $0 \leq k3 \leq 9$, and $3 \leq k1+k2+k3 \leq 10$.

According to preferred embodiments of the above present invention, provided are the aforementioned phospholipid derivative, wherein the condition $4 \leq k1+k2+k3 \leq 8$ is satisfied; the aforementioned phospholipid derivative, wherein $R^1CO$ and $R^2CO$ independently represent an acyl group having from 12 to 20 carbon atoms; the aforementioned phospholipid derivative, wherein k2 is 0; the aforementioned phospholipid derivative, wherein "a" and "b" represent 0; and the aforementioned phospholipid derivative, wherein the following conditions k3<1 and k2>k3 are satisfied.

From another aspect of the present invention, provided are a surfactant comprising a phospholipid derivative represented by the aforementioned general formula (1); a solubilizer comprising a phospholipid derivative represented by the aforementioned general formula (1); a dispersing agent, preferably a dispersing agent for cosmetics, comprising a phospholipid derivative represented by the aforementioned general formula (1); and a lipid membrane structure, preferably liposome, comprising a phospholipid derivative represented by the aforementioned general formula (1).

From a further aspect of the present invention, provided is a method for producing a phospholipid derivative represented by the aforementioned general formula (1), which comprises the step of reacting a phospholipid compound represented by the following general formula (2):

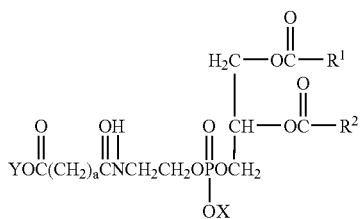

(2)

wherein $R^1CO$ and $R^2CO$ independently represent an acyl group having from 8 to 22 carbon atoms; X represents hydrogen atom, an alkali metal atom, ammonium or an organic ammonium; "a" represents an integer of from 0 to 4; and Y represents hydrogen atom or N-hydroxysuccinimide, and a polyalkylene oxide compound represented by the following general formula (3):

$$Z\text{-}[\text{---}O(AO)_m\text{---}H]_k \quad (3)$$

wherein Z represents a residue of a compound having from 3 to 10 hydroxyl groups; AO represents one or two or more kinds of oxyalkylene groups having from 2 to 4 carbon atoms, and when AO represents two or more kinds of oxyalkylene groups, they may bond to form a block copolymer or random copolymer; "m" represents an average number of moles of the oxyalkylene group added; and m and k are numbers satisfying the following conditions: $3 \leq m \leq 200$, $9 \leq m \times k \leq 1000$, and $3 \leq k \leq 10$, in an organic solvent in the presence of a basic catalyst (this step is also referred to as "Step A"). This method can be preferably performed at a temperature in the range of from 20 to 90° C., and is preferably performed in the presence of a dehydrocondensing agent.

Further, also provided is a method for producing a phospholipid derivative represented by the aforementioned general formula (1), which comprises the step of reacting a polyalkylene oxide derivative represented by the following general formula (4):

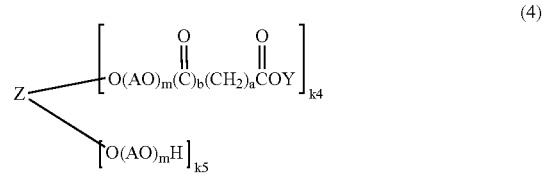

(4)

wherein Z represents a residue of a compound having from 3 to 10 hydroxyl groups; "a" represents an integer of from 0 to 4; "b" represents 0 or 1; "m" represents an average number of moles of the oxyalkylene group added; Y represents hydrogen atom or N-hydroxysuccinimide; and k4 and k5 are numbers satisfying the following conditions: $1 \leq k4 \leq 10$, $0 \leq k5 \leq 9$, and $3 \leq k4+k5 \leq 10$, and a phospholipid derivative represented by the following general formula (5):

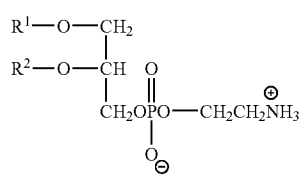

(5)

wherein $R^1CO$ and $R^2CO$ have the same meanings as those defined in the aforementioned formula (1), in organic solvents in the presence of a basic catalyst. This method can be preferably performed at a temperature in the range of from 20 to 90° C.

BEST MODE FOR CARRYING OUT THE INVENTION

In the phospholipid derivatives of the present invention represented by the formula (1), Z is a residue of a compound having from 3 to 10 hydroxyl groups. A type of the compound having from 3 to 10 hydroxyl groups is not particularly limited. Examples include, for example, glycerin, polyglycerin compounds such as diglycerin, pentaerythritol, triglycerin, tetraglycerin, pentaglycerin, hexaglycerin, heptaglycerin, and octaglycerin. In the specification, the residue of a compound having from 3 to 10 hydroxyl groups means a residual portion of the compound obtained by eliminating hydroxyl groups of a total number (k1+k2+k3) wherein each of k1, k2 and k3 represents arms.

The value of k1+k2+k3 corresponds to the number of arms on Z, and the number is an integer in the range of from 3 to 10, preferably from 3 to 8, more preferably from 4 to 8 (the numerical ranges indicated with "from—to" in the specification are ranges including numerical values of upper and lower limits). When the number of arms is less than 3, the desired effect of the compounds may sometimes not be obtained. When the number of arms is more than 10, viscosity of multi-arm raw materials, including polyglycerine and the like as typical examples, becomes high, which causes difficulty in handling the materials. In addition, the raw materials may sometimes be hardly obtainable.

The symbol k1 represents the number of a partial structure, containing a residue of a phospholipid compound represented by the formula (2), that bonds to a residue represented by Z, and the number is 1 or 2. When the number of the partial structure containing the aforementioned phospholipid compound is 0, the compound cannot stably bind to lipid bilayer membranes such as those of liposomes because no hydrophobic bond portion exists. Therefore, modification of liposome membranes with such a compound may become difficult. Further, when the number of the partial structure containing the aforementioned phospholipid compound is larger than 2, many phospholipid residues are contained in a single molecule, and hydrophobic bonding power to liposome membranes may become stronger. Therefore, the degree of freedom of the polyoxyethylene chain may become small, and thus the desired effect of the compounds of the present invention may sometimes not be obtained.

$R^1CO$ and $R^2CO$ independently represent an acyl group having from 8 to 22 carbon atoms, preferably from 12 to 20 carbon atoms, more preferably from 14 to 18 carbon atoms. A type of the acyl group is not particularly limited, and any of an aliphatic acyl group or an aromatic acyl group may be used. In general, an acyl group derived from an aliphatic acid may preferably be used. Specific examples of $R^1CO$ and $R^2CO$ include, for example, acyl groups derived from saturated or unsaturated linear or branched aliphatic acids such as caprylic acid, capric acid, lauric acid, myristic acid, palmitic acid, palmitoleic acid, stearic acid, isostearic acid, oleic acid, linolic acid, arachic acid, behenic acid, erucic acid and lignoceric acid. $R^1CO$ and $R^2CO$ may be the same or different. When the carbon number of $R^1CO$ and $R^2CO$ exceeds 22, dispersibility of the compounds in an aqueous phase may become poor, and reactivity may sometimes be lowered. When the carbon number is less than 8, the crystallinity may become poor in a purification step, and a final purity of a target substance may become low.

Symbol k2 represents the number of the partial structure, of which end is represented by —COOX, that bonds to a residue represented by Z, and the number is chosen from the range of from 0 to 9. When the number is 0, it is meant that no partial structure of which end is represented by —COOX substantially exists in the compounds of the present invention. X represents hydrogen atom, an alkali metal atom, ammonium or an organic ammonium, preferably hydrogen atom or an alkali metal atom. Specific examples of the alkali metal atom include sodium, potassium and the like, and specific examples of the organic ammonium include triethylammonium and the like.

Symbol k3 represents the number of the partial structure, of which end is hydroxyl group or methyl group, that bonds to a residue represented by Z, and the number is chosen from the range of from 0 to 9. Q is hydrogen atom or methyl group. When Q is an alkyl group other than methyl group, hydrophilicity of the compounds of the present invention may sometimes be lost.

Symbol b is an integer of 0 or 1, and when "b" is 1, "a" is preferably an integer of from 1 to 4, more preferably 2 or 3. When "b" is 0, "a" is preferably 1 or 0, more preferably 0.

The oxyalkylene group represented by AO is an oxyalkylene group having from 2 to 4 carbon atoms, preferably 2 or 3 carbon atoms, and examples include, for example, oxyethylene group, oxypropylene group, oxytrimethylene group, oxybutylene group and the like. Among them, oxyethylene group and oxypropylene group are preferred, and oxyethylene group is particularly preferred. The oxyalkylene groups that constitute the polyoxyalkylene group represented by $-(AO)_m-$ may consist of a single kind of oxyalkylene groups. Alternatively, they may consist of a combination of two or more kinds of oxyalkylene groups. When two or more kinds of oxyalkylene groups are combined, a manner of combination is not particularly limited, and the polyoxyalkylene group may be a block or random copolymer. When a ratio of oxyethylene groups based on total oxyalkylene groups is low, water solubility may sometimes be lowered. Therefore, the ratio of oxyethylene groups based on the total oxyalkylene groups is preferably from 50 to 100 mole %.

Symbol m represents an average number of moles of the oxyalkylene group added, and the number is from 8 to 200, preferably from 7 to 80. When m is smaller than 3, a desired effect of the phospholipid derivatives of the present invention, as used in a drug delivery system, may be reduced. When the number is larger than 200, reactivity between a phospholipid compound represented by the formula (2) and a polyalkylene oxide compound represented by the formula (3) may be reduced in the preparation of the phospholipid derivatives of the present invention, and viscosity of a polyalkylene oxide compound represented by the formula (3) may be increased, which may sometimes result in degradation of workability. In addition, symbol m means the number of oxyalkylene groups contained in polyoxyalkylene group existing in each of [k1+k2+k3] of arms contained in compounds of the present invention. Formula m×[k1+k2+k3] means the number of oxyalkylene groups contained in the compounds of the present invention as a whole, and the number is from 9 to 1000, preferably from 20 to 700, more preferably from 30 to 350.

The method for producing the compounds of the present invention represented by the formula (1) is not particularly limited. The phospholipid derivatives wherein k2 is 0 can be produced, for example, by Step A with a high purity. In the phospholipid compounds represented by the formula (2) used in Step (A), $R^1CO$, $R^2CO$ and "a" are the same as those explained in the formula (1), and Y is hydrogen atom or N-hydroxysuccinimide.

The phospholipid compounds represented by the formula (2) can be produced by a known method. For example, the compounds can be easily produced by reacting a phospholipid compound with a dicarboxylic acid anhydride as described later. The phospholipid to be used may be a natural phospholipid or a synthetic phospholipid, and examples include, for example, synthetic and natural phosphatidyldiethanolamines such as soybean phosphatidyldiethanolamine, hydrogenated soybean phosphatidyldiethanolamine, egg yolk phosphatidyldiethanolamine and hydrogenated egg yolk phosphatidyldiethanolamine, and the like.

In the polyalkylene oxide compounds represented by the formula (3) used in Step (A), Z, AO and m are the same as those explained as for the formula (1). Symbol k corresponds to the sum of k1, k2 and k3, each explained as for the formula (1). The reaction of a polyalkylene oxide compound represented by the formula (3) and a phospholipid compound represented by the formula (2) can be performed in organic solvents in the presence of a basic catalyst, and the reaction can be generally carried out by using a dehydrocondensing agent.

A type of the basic catalyst is not particularly limited. Examples include, for example, as nitrogen-containing substances, triethylamine, pyridine, dimethylaminopyridine, ammonium acetate and the like, as organic salts, sodium phosphate, sodium carbonate, sodium hydrogencarbonate, sodium borate, sodium acetate and the like. The amount of the basic catalyst is, for example, from 1.5 to 10 moles, preferably from 2 to 5 moles, per mole of the polyalkylene oxide compound represented by the formula (3). As the organic solvent, those not having a reactive functional group such as hydroxyl group can be used without any particular limitation. Examples include, for example, ethyl acetate, dichloromethane, chloroform, benzene, toluene and the like. Among them, chloroform and toluene are preferred. Organic solvents having hydroxyl group, such as ethanol, may sometimes react with the carboxyl group at the end of the phospholipid compound represented by the formula (2).

When a dehydrocondensing agent is used, those achieving dehydration condensation of the hydroxyl group of the polyalkylene oxide compound represented by the formula (3) and a carboxylic acid group of the phospholipid represented by the formula (2) can be used without any particular limitation. Examples of such dehydrocondensing agents include carbodiimide derivatives such as dicyclohexylcarbodiimide, and dicyclohexylcarbodiimide is particularly preferred. The amount of the dehydrocondensing agent used is, for example, desirably from 1.05 to 5 moles, preferably from 1.5 to 2.5 moles, per mole of the polyalkylene oxide compound represented by the formula (3). An yield may sometimes be increased by adding N-hydroxysuccinimide to the reaction system in an amount of from 0.1 to 2 moles per mole of the polyalkylene oxide compound represented by the formula (3).

The reaction temperature of Step (A) is usually in the range of from 20 to 90° C., preferably from 40 to 80° C. The reaction time is desirably 1 hour or more, preferably from 2 to 8 hours. At a temperature lower than 20° C., a reactivity may sometimes become lowered, and at a temperature higher than 90° C., the acyl group of the phospholipid compound represented by the formula (2) used for the reaction may sometimes be hydrolyzed.

The compounds of the present invention represented by the formula (1) can also be produced by reacting an activated ester derivative of the phospholipid compound represented by the formula (2) and a polyalkylene oxide compound represented by the formula (3). The aforementioned activated ester derivative can be obtained by reacting, for example, a phospholipid compound represented by the formula (2) and an activating agent in the presence of a dehydrocondensing agent. A type of the aforementioned activating agent is not particularly limited, and examples include, for example, N-hydroxysuccinimide, N,N'-disuccinimide carbonate, 1-hydroxybenzotriazole, N-hydroxy-5-norbornene-2,3-dicarboxyimide, N-hydroxyphthalimide, 4-hydroxyphenyldimethylsulfonium methyl sulfate, isobutyl chloroformate and the like. Among these, N-hydroxysuccinimide is preferred.

The reaction of the phospholipid compound represented by the formula (2) and the activating agent can be performed, for example, at a reaction temperature of from 15 to 80° C., preferably from 25 to 55° C. in the presence of a dehydrocondensing agent in a solvent that does not react with carboxylic acids, such as chloroform and toluene, in the same manner as the reaction with a dicarboxylic acid anhydride. The reaction can be performed by, for example, dispersing the activating agent in a solution of the polyalkylene oxide compound and stirring the dispersion. For example, when N-hydroxysuccinimide is used as the activating agent, the carboxyl group of the phospholipid compound represented by the formula (2) and the hydroxyl group of N-hydroxysuccinimide react to give an activated ester derivative consisting of the phospholipid compound represented by the formula (2) to which N-hydroxysuccinimide bonds at the end of the carboxyl group side of the phospholipid compound represented by the formula (2).

The phospholipid derivatives of the formula (1) wherein k2 is not 0, i.e., the compounds which have the partial structure of branching oxyalkylene group having carboxyl group at the end, can be produced with a high purity by reacting a polyalkylene oxide derivative represented by the aforementioned general formula (4) and a phospholipid derivative represented by the aforementioned general formula (5) in an organic solvent in the presence of a basic catalyst.

As the organic solvent used for the reaction, those not having a reactive functional group such as hydroxyl group can be used without any particular limitation. Examples include, for example, ethyl acetate, dichloromethane, chloroform, benzene, toluene and the like. Among them, chloroform and toluene are preferred. Organic solvents having hydroxyl group such as ethanol may sometimes react with the carboxyl group at the end of the polyalkylene oxide compound represented by the formula (4).

A type of the basic catalyst used for the reaction is not particularly limited. Examples include, for example, as nitrogen-containing substances, triethylamine, ammonium acetate and the like, as organic salts, sodium phosphate, sodium carbonate, sodium hydrogencarbonate, sodium borate, sodium acetate and the like. The amount of the basic catalyst is, for example, from 1.5 to 10 moles, preferably from 2 to 7 moles, per mole of the polyalkylene oxide compound represented by the formula (4). The reaction temperature is usually from 20 to 90° C., preferably from 40 to 80° C. The reaction time is 1 hour or more, preferably from 2 to 8 hours. At a temperature lower than 20° C., a reactivity may sometimes become lowered, and at a temperature higher than 90° C., the acyl group of the phospholipid compound represented by the formula (5) used for the reaction may sometimes be hydrolyzed. The compounds of the present invention may be obtained as a single kind of compound, or alternatively, may be obtained as a mixture of compounds having different numbers for each of k1, k2 and k3 depending on the synthetic procedures. Such a mixture is also fall within the scope of the present invention.

By using the compounds of the present invention represented by the aforementioned general formula (1) as surfactants, a solubilized solution, an emulsion, and a dispersion can be obtained. When the surfactant of the present invention is used as an emulsifier, a solubilizer, or a dispersing agent, the emulsifier, solubilizer, or dispersing agent may solely contain the surfactant of the present invention, or alternatively, the emulsifier, solubilizer or dispersing agent may contain other known ingredients which are used for emulsification, solubilization, or dispersion. A form of the solubilized solution or dispersion is not limited. Examples include solutions in which a fat-soluble substance or the like is dissolved in a medium such as water and buffers, dispersions in which a fat-soluble substance or the like is dispersed in a medium such as water and buffers, and the like.

A form of the emulsion or solubilized solution is not limited. Examples include micellar solutions formed with the surfactant of the present invention, i.e., micellar solutions in which a fat-soluble substance is contained in micelles, emulsion solutions in which dispersed particles, which are formed with the surfactant of the present invention and a fat-soluble substance or the like, exist in a dispersion medium such as water and buffers as colloidal particles or larger particles. Examples of the micellar solutions include, in particular, polymer micellar solutions in which dispersed particles have a diameter of 10 to 300 nm. The emulsion solutions may an O/W type emulsion in which a fat-soluble substance is added to an oil phase, or a W/O/W type emulsion in which a fat-soluble substance is added to an aqueous phase. The fat-soluble substance that can be solubilized or emulsified is not particularly limited. Examples include, for example, higher alcohols, ester oils, triglycerin, tocopherol, higher fatty acids, phospholipids, hardly soluble medicaments such as adriamycin, cisplatin, paclitaxel, and amphotericin B. An application as a dispersing agent in the cosmetic field is also not particularly limited. When a water-soluble substance such as ascorbic acid should be retained in an internal aqueous phase of a lipid membrane structure, or when a fat-soluble substance such as tocopherol should be retained in a lipid bilayer membrane, the objective substance can be more stably dispersed in an aqueous solution by using the compounds of the present invention as an agent for forming a lipid membrane structure. When the subject compounds are used as surfactants or dispersing agents, an amount of 0.1 to 20% by weight, preferably 0.5 to 7% by weight, more preferably 0.5 to 5% by weight, may be used based on the total weight of the substances to be solubilized, dispersed, emulsified or the like.

The compounds of the aforementioned general formula (1) wherein k2 is 0 can be effectively used, in particular, as nonionic surfactants under a high salt concentration. Polyalkylene oxide-modified phospholipids and the like generally have hydrophilicity deriving from oxyalkylene groups and hydrophobicity deriving from acyl groups, and accordingly, they can be used as surfactants. However, the surfactants having oxyalkylene groups, including polyalkylene oxide-modified phospholipids as typical examples, generally have a problem in that they generate turbidity when used under a condition of a high salt concentration. Moreover, although a use of nonionic surfactants consisting of glycidol derivatives under a high salt concentration condition was reported, such use causes problems of skin irritation due to remaining glycidyl compounds and the like, and accordingly, they have a problem in that they are not suitable for use in the cosmetic field. The compounds of the aforementioned general formula (1) wherein Q is hydrogen atom have a characteristic property that they can maintain a high solubilizing ability even under a high salt concentration condition, and can be used as surfactants having superior salt tolerance. They can also be used as surfactants having superior compatibility with skins in the cosmetic field.

The compounds of the aforementioned general formula (1) wherein k3<1 and k2>k3, i.e., the compounds having carboxyl group at the end of the arms of polyoxyalkylene chain, can be used, for example, as dispersing agents as pH-sensitive phospholipids. When a cationic substance (e.g., cationic physiologically active substances and the like), basic substance or the like is dispersed in water, stable dispersion in water can be obtained by coating the surfaces of microparticles containing the cationic substance, basic substance or the like with the aforementioned compounds. The compounds of the present invention have a polyanionic group, and accordingly, they can provide stable dispersion on the basis of ionic bonds. When Q is hydrogen atom, and both of k2 and k3 are 1 or more, carboxyl groups and the like coexist with hydroxyl groups, and such compounds may be crosslinked by intermolecular bonds and gelled during a manufacturing process. For this reason, when the compounds are used as anionic dispersing agents, k3 is preferably smaller than 1.

The compounds of the present invention represented by the aforementioned general formula (1) can be used as phospholipids constituting lipid membrane structures such as liposomes, emulsions, and micelles. By using the compounds of the present invention, circulation time in blood of lipid membrane structures, preferably liposomes, can be increased. This effect can be attained by adding a small amount of the compounds of the present invention to the lipid membrane structures. Although it is not intended to be bound by any specific theory, by using the compounds of the present invention having three or more arms as a phospholipid constituting a lipid membrane structure, aggregation of microparticles in an aqueous solution is prevented, and a stable dispersed state is attained, because the polyoxyethylene chains have three-dimensional bulkiness in the membranes of the lipid membrane structures.

An amount of the compounds of the present invention mixed in lipid membrane structures may be an amount sufficient for effective expression of efficacy of a medicament in a living body, and the amount is not particularly limited. For example, the amount can be suitably chosen depending on a type of a medicament to be contained in lipid membrane structures, a purpose of use such as therapeutic use and prophylactic use, a form of lipid membrane structures and the like. A type of a medicament contained in lipid membrane structures provided by the present invention is not particularly limited. For example, compounds used as antitumor agents are preferred. Examples of such compounds include, for example, irinotecan hydrochloride, nogitecan hydrochloride, exatecan, RFS-2000, Lurtotecan, camptothecin derivatives such as BNP-1350, Bay-383441, PNU-166148, IDEC-132, BN-80915, DB38, DB-81, DB-90, DB-91, CKD-620, T-0128, ST-1480, ST-1481, DRF-1042 and DE-310, docetaxel hydrate, paclitaxel, taxane derivatives such as IND-5109, BMS-184476, BMS-188797, T-3782, TAX-1011, SB-RA-31012, SBT-1514 and DJ-927, ifosphamide, nimustine hydrochloride, carboquone, cyclophosphamide, dacarbazine, thiotepa, busulfan, melphalan, ranimustine, estramustine phosphate sodium, 6-mercaptopurine riboside, enocitabine, gemcitabine hydrochloride, carmofur, cytarabine, cytarabine ocphossfate, tegafur, doxifluridine, hydroxycarbamide, fluorouracil, methotrexate, mercaptopurine, fludarabine phosphate, actinomycin D, aclarubicin hydrochloride, idarubicin hydrochloride, epirubicin hydrochloride, daunorubicin hydrochloride, doxorubicin hydrochloride, pirarubicin hydrochloride, bleomycin hydrochloride, zinostatin stimalamer, neocarzinostatin, mitomycin C, bleomycin sulfate, peplomycin sulfate, etoposide, vinorelbine ditartrate, vincristine sulfate, vindesine sulfate, vinblastine sulfate, amrubicin hydrochloride, gefitinib, exemestane, capecitabine, TNP-470, TAK-165, KW-2401, KW-2170, KW-2871, KT-5555, KT-8391, TZT-1027, S-3304, CS-682, YM-511, YM-598, TAT-59, TAS-101, TAS-102, TA-106, FK-228, FK-317, E7070, E7389, KRN-700, KRN-5500, J-107088, HMN-214, SM-11355, ZD-0473 and the like.

Further, a gene or the like may be encapsulated in the lipid membrane structures of the present invention. The gene may be any of oligonucleotide, DNA, and RNA, and examples include, in particular, genes for in vitro gene transfer such as transformation, genes acting upon in vivo expression, for example, genes for gene therapies and genes used for breeding of industrial animals such as laboratory animals and farm animals. Examples of the genes for gene therapies include antisense oligonucleotides, antisense DNAs, antisense RNA., genes coding for physiologically active substances such as enzymes and cytokines, and the like.

The aforementioned lipid membrane structures may be further added with phospholipids, sterols such as cholesterol and cholestanol, other aliphatic acids having a saturated or unsaturated acyl group of 8 to 22 carbon atoms, and antioxidants such as α-tocopherol in addition to the compound of the present invention. Examples of the phospholipids include phosphatidylethanolamine, phosphatidylcholine, phosphatidylserine, phosphatidylinositol, phosphatidylglycerol, cardiolipin, sphingomyelin, ceramide phosphorylethanolamine, ceramide phosphorylglycerol, ceramide phosphorylglycerol phosphate, 1,2-dimyristoyl-1,2-deoxyphosphatidylcholine, plasmalogen, phosphatidic acid and the like, and these substances can be used alone or in combination of two or more kinds. The aliphatic acid residues of these phospholipids are not particularly limited. Examples include saturated or unsaturated aliphatic acid residues having 12 to 20 carbon atoms, and specific examples include, for example, acyl groups derived from aliphatic acids such as lauric acid, myristic acid, palmitic acid, stearic acid, oleic acid, and linolic acid. Moreover, phospholipids derived from natural products such as egg yolk lecithin and soybean lecithin can also be used.

Forms of lipid membrane structures containing the compounds of the present invention and methods for preparation thereof are not particularly limited. Examples of available forms thereof include, for example, forms of dried lipid mixtures, forms of dispersions in aqueous solvents, dried or solidified forms of these and the like. When a preparation in a form of dried lipid mixture is desired, the form can be prepared by, for example, once dissolving lipid components to be used in an organic solvent such as chloroform and then subjecting the solution to solidification under reduced pressure using an evaporator or to spray-drying by using a spray dryer. Examples of the lipid membrane structures dispersed in an aqueous solvent include single membrane liposomes, multilayer liposomes, O/W type emulsions, W/O/W type emulsions, spherical micelles, fibrous micelles, layered structures of irregular shapes and the like. Among them, liposomes are preferred. A size of the lipid membrane structures in a dispersed state is not particularly limited. For example, liposomes and emulsions may have a particle diameter of 50 nm to 5 µm, and spherical micelles may have a particle diameter of 5 nm to 100 nm. As for fibrous micelles and layered structures of irregular shapes, they are considered to be constructed with layers which has a thickness of 5 to 10 nm per layer.

Components of the aqueous solvent (medium) is also not particularly limited, and the medium may be a buffer such as phosphate buffer, citrate buffer and phosphate buffered physiological saline, physiological saline, cell culture medium or the like. When the compounds of the present invention are used in an aqueous solvent, the lipid membrane structures can be stably dispersed. Besides water, an aqueous solution of saccharide such as glucose, lactose and sucrose, an aqueous solution of polyhydric alcohol such as glycerin and propylene glycol or the like may be added. In order to stably store the lipid membrane structures dispersed in such an aqueous solvent for a long period of time, it is desirable to eliminate electrolytes in the aqueous solvent as low as possible from a viewpoint of physical stability, for example, prevention of aggregation. Moreover, from a viewpoint of chemical stability of lipids, it is desirable to adjust pH of the aqueous solvent to be within the range of weakly acidic to approximately neutral pH (pH 3.0 to 8.0), or to remove dissolved oxygen by nitrogen babbling. Further, when the lipid membrane structures are stored after lyophilization or spray drying, for example, use of each of a saccharide aqueous solution and a polyhydric alcohol aqueous solution in lyophilization of a saccharide aqueous solution may achieve effective preservation. A concentration of these aqueous solvents is not particularly limited. For example, the concentration of the saccharide aqueous solution may preferably be 2 to 20% (W/V), more preferably 5 to 10% (W/V). Also for example, the concentration of the polyhydric alcohol aqueous solution may preferably be 1 to 5% (W/V), more preferably 2 to 2.5% (W/V). In the buffers, a concentration of buffering agent may preferably be 5 to 50 mM, more preferably 10 to 20 mM. A concentration of the lipid membrane structures in the aqueous solvent is not particularly limited. The concentration of the total lipids in the lipid membrane structures may preferably be 0.1 to 500 mM, more preferably 1 to 100 mM.

The lipid membrane structures in a form of a dispersion in an aqueous solvent can be prepared by adding the aforementioned dried lipid mixture to the aqueous solvent and emulsifying the mixture by using an emulsifier such as homogenizer, ultrasonic emulsifier, high-pressure injection emulsifier or the like. They can also be produced by a method well known as a method for producing liposomes, for example, the reverse phase evaporation method or the like, and the methods are not particularly limited. When a control of the size of the lipid membrane structures is desired, extrusion (extrusion filtration) can be performed under a high pressure by using a membrane filter having uniform pore sizes.

Examples of a method for further drying the aforementioned lipid membrane structures dispersed in an aqueous solvent include ordinary lyophilization and spray drying. As the aqueous solvent used for these methods, an aqueous solution of saccharide, preferably aqueous solution of sucrose or aqueous solution and lactose, may be used as described above. When lipid membrane structures dispersed in an aqueous solvent are once produced and further dried, long-term storage of the lipid membrane structures becomes possible. In addition, when an aqueous solution of a medicament is added to such dried lipid membrane structures, the lipid mixture is efficiently hydrated, and thus an advantage is provided that a medicament can be efficiently retained in the lipid membrane structures. By adding a medicament to the lipid membrane structures, a pharmaceutical composition can be produced, and the resulting lipid membrane structures can be used as a pharmaceutical composition for therapeutic treatment and/or prophylactic treatment of a disease. When the medicament is a gene, the composition can be used for a kit for gene transfer.

As for a form of the pharmaceutical composition, the form may be the lipid membrane structures retaining a medicament, as well as a mixture of a medicament and the lipid membrane structures. The term "retain" used herein means that a medicament exists inside the membranes of the lipid membrane structures, on the membrane surfaces, in the membranes, in the lipid layers, and/or on the lipid layer surfaces. An available form of the pharmaceutical composition and a method for preparation thereof are not particularly limited in the same manner as the lipid membrane structures. As for the available form, examples include a form of a dried mixture, a form of a dispersion in an aqueous solvent, and forms obtained by further drying or freezing said forms.

A dried mixture of lipids and a medicament can be produced by, for example, once dissolving lipid components and a medicament to be used in an organic solvent such as chloroform and then subjecting the resulting solution to solidification under reduced pressure by using an evaporator or spray drying by using a spray dryer. Examples of a form in which a mixture of lipid membrane structures and a medicament are dispersed in an aqueous solvent include, but not particularly limited thereto, multi-layer liposomes, single membrane liposomes, O/W type emulsions, W/O/W type emulsions, spherical micelles, fibrous micelles, layered structures of irregular shapes and the like. A size of particles (particle diameter) as the mixture, a composition of the aqueous solvent and the like are not particularly limited. For example, liposomes may have a size of 50 nm to 2 µm, spherical micelles may have a size of 5 to 100 nm, and emulsions may have a particle diameter of 50 nm to 5 µm. A concentration of the mixture in the aqueous solvent is also not particularly limited. Several methods are known as methods for producing a mixture of lipid membrane structures and a medicament in the form of dispersion in an aqueous solvent. It is necessary to appropriately chose a suitable method depending on an available form of the mixture of lipid membrane structures and a medicament.

Production Method 1

Production Method 1 is a method of adding an aqueous solvent to the aforementioned dried mixture of lipids and a medicament and emulsifying the mixture by using an emulsifier such as homogenizer, ultrasonic emulsifier, high-pressure injection emulsifier, or the like. If it is desired to control the size (particle diameter), extrusion (extrusion filtration) can be further performed under a high pressure by using a membrane filter having uniform pore sizes. In this method, in order to prepare a dried mixture of lipids and a medicament first, it is necessary to dissolve the medicament in an organic solvent, and the method has an advantage that it can make the best utilization of interactions between the medicament and lipid membrane structures. Even when the lipid membrane structures have a multi-layer structure, a medicament can enter into the inside of the multiple layers, and thus use of this method generally provides a higher retention ratio of the medicament in the lipid membrane structures.

Production Method 2

Production Method 2 is a method of adding an aqueous solvent containing a medicament to dried lipid components obtained by dissolving the lipid components in an organic solvent and evaporating the organic solvent, and emulsifying the mixture. If it is desired to control the size (particle diameter), extrusion (extrusion filtration) can be further performed under a high pressure by using a membrane filter having uniform pore sizes. This method can be used for a medicament that is hardly dissolved in an organic solvent, but can be dissolved in an aqueous solvent. When the lipid membrane structures are liposomes, they have an advantage that they can retain a medicament also in the part of internal aqueous phase.

Production Method 3

Production Method 3 is a method of further adding an aqueous solvent containing a medicament to lipid membrane structures such as liposomes, emulsions, micelles or layered structures already dispersed in an aqueous solvent. This method is limitedly applied to a water-soluble medicament. The addition of a medicament to already prepared lipid membrane structures is performed from the outside. Therefore, if the medicament is a polymer, the medicament cannot enter into the inside of the lipid membrane structures, and the medicament may be present in a form that it binds to the surfaces of lipid membrane structures. When liposomes are used as the lipid membrane structures, use of Production Method 3 may result in formation of a sandwich-like structure in which the medicament is sandwiched between liposome particles (generally called as a complex). An aqueous dispersion of lipid membrane structures alone is prepared beforehand in this production method. Therefore, decomposition of a medicament during the preparation need not be taken into consideration, and a control of the size (particle diameter) is also readily operated, which enables relatively easier preparation compared with Production Methods 1 and 2.

Production Method 4

Production Method 4 is a method of further adding an aqueous solvent containing a medicament to a dried product obtained by once producing lipid membrane structures dispersed in an aqueous solvent and then drying the same. In this method, a medicament is limited to a water-soluble medicament in the same manner as Production Method 3. A significant difference from Production Method 3 is a mode of presence of the lipid membrane structures and a medicament. That is, in Production Method 4, lipid membrane structures dispersed in an aqueous solvent are once produced and further dried to obtain a dried product, and at this stage, the lipid membrane structures are present in a state of a solid as fragments of lipid membranes. In order to allow the fragments of lipid membranes to be present in a solid state, it is preferable to use an aqueous solution of a saccharide, preferably an aqueous solution of sucrose or aqueous solution of lactose, as the aqueous solvent as described above. In this method, when the aqueous solvent containing a medicament is added, hydration of the fragments of the lipid membranes present in a state of a solid quickly starts with the invasion of water, and thus the lipid membrane structures can be reconstructed. At this time, a structure of a form in which a medicament is retained in the inside of the lipid membrane structures can be produced.

In Production Method 3, when a medicament is a polymer, the medicament cannot enter into the inside of the lipid membrane structures, and is present in a mode that it binds to the surfaces of the lipid membrane structures. Production Method 4 significantly differs in this point. In Production Method 4, an aqueous dispersion of lipid membrane structures alone is prepared beforehand, and therefore, decomposition of the medicament during the emulsification need not be taken into consideration, and a control of the size (particle diameter) is also easy attainable. For this reason, said method enables relatively easier preparation compared with Production Methods 1 and 2. Besides the above mentioned advantages, this method also has advantages that storage stability for a pharmaceutical preparation is easily secure, because the method uses lyophilization or spray drying; when the dried preparation is rehydrated with an aqueous solution of a medicament, original size (particle diameter) can be reproduced; when a polymer medicament is used, the medicament can be easily retained in the inside of the lipid membrane structures and the like.

As other method for producing a mixture of lipid membrane structures and a medicament in a form of a dispersion in an aqueous solvent, a method well known as that for producing liposomes, e.g., the reverse phase evaporation method or the like, may be separately used. If it is desired to control the size (particle diameter), extrusion (extrusion filtration) can be performed under a high pressure by using a membrane filter having uniform pore sizes. Further, examples of the method for further drying a dispersion, in which the aforementioned mixture of lipid membrane structures and a medicament is dispersed in an aqueous solvent, include lyophilization and spray drying. As the aqueous solvent in this process, it is preferable to use an aqueous solution of a saccharide, preferably an aqueous solution of sucrose or an aqueous solution of lactose. Examples of the method for further freezing a dispersion, in which the aforementioned mixture of lipid membrane structures and a medicament is dispersed in an aqueous solvent, include ordinary freezing methods. As the aqueous solvent in this process, it is preferable to use an aqueous solution of saccharide or aqueous solution of polyhydric alcohol in the same manner as the solution for the lipid membrane structures alone.

Lipids that can be added to the pharmaceutical composition may be suitably chosen depending on a type of a medicament to be used and the like. The lipids are used in an amount of, for example, 0.1 to 1000 parts by weight, preferably 0.5 to 200 parts by weight, based on 1 part by weight of a medicament when the medicament is not a gene. When the medicament is a gene, the amount is preferably 1 to 500 nmol, more preferably 10 to 200 nmol, with 1 μg of a medicament (gene).

The method for use of the compounds and the pharmaceutical composition of the present invention may be suitably considered depending on a mode of usage. The administration route for humans is not particularly limited, and either oral administration or parenteral administration may be used. Examples of dosage forms for oral administration include, for example, tablets, powders, granules, syrups, capsules, solutions for internal use and the like, and examples of dosage forms for parenteral administration Include, for example, injections, drip infusion, eye drops, ointments, suppositories, suspensions, cataplasms, lotions, aerosols, plasters and the like. In the medicinal field, injections and drip infusion are preferred among them, and as the administration method, intravenous injection, subcutaneous injection and intradermal injection, as well as local injection to targeted cells or organs are preferred. Further, as for the cosmetic field, examples of forms of cosmetics include lotions, creams, toilet water, milky lotions, foams, foundations, lipsticks, packs, skin cleaning agents, shampoos, rinses, conditioners, hair tonics, hair liquids, hair creams and the like.

The administration route of the pharmaceutical composition is not particularly limited, and either oral administration or parenteral administration may be used. Parenteral administration is preferred. The form of the pharmaceutical composition is also not particularly limited. Examples of dosage forms for oral administration include, for example, tablets, powders, granules, syrups and the like, and examples of dosage forms for parenteral administration include, for example, injections, drip infusion, eye drops, ointments, suppositories and the like. Among them, injections and drip infusion are preferred, and as the administration method, intravenous injection as well as local injection to targeted cells or organs are preferred.

EXAMPLES

The present invention will be explained more specifically with reference to the following examples. However, the scope of the present invention is not limited to these examples.

Synthesis Example 1

Synthesis of Polyoxyethylene Pentaerythritol Ether (Average Molecular Weight: 2000)-mono-distearoylphosphadylethanolamine Succinate Preparation of Distearoylphosphatidylethanolamine Succinate Distearoylphosphatidylethanolamine (748 mg, 1 mmol) was added with chloroform (50 mL), stirred at 40° C. and further added with triethylamine (100 mg, 1 mmol) to obtain a phospholipid chloroform solution. This solution was added with succinic anhydride (105 mg, 1.05 mmol) and reacted at 40° C. for 2 hours. The end point of the reaction was determined by TLC described below as a point at which distearoylphosphatidylethanolamine became no longer detectable by ninhydrin coloration. The reaction mixture was cooled and then filtered to remove unreacted distearoylphosphatidylethanolamine. The filtrate was added with acetone (100 mL) to obtain crystals of distearoylphosphatidylethanolamine succinate (805 mg). Synthesis of polyoxyethylene pentaerythritol Ether (average molecular weight: 2000)-mono-distearoylphosphadylethanolamine Succinate Preparation of Polyoxyethylene Pentaerythritol Ether (Average Molecular Weight: 2000)-mono-distearoyl-phosphatidyl ethanolamine succinate Polyoxyethylene pentaerythritol ether (average molecular weight: 2000, m=11, 2.1 g, 1.05 mol) was added with chloroform (20 mL) and dissolved, and then warmed to 40° C. to obtain a uniform solution. Then, distearoylphosphatidylethanolamine succinate obtained in the above (1) was dissolved in chloroform (10 mL), added with triethylamine (100 mg, 1 mmol), and added with the solution made uniform by warming to 40° C. The mixture was added with N-hydroxysuccinimide (1.24 g, 0.011 mol) and dicyclohexylcarbodiimide (4.25 g, 0.021 mol) and reacted at room temperature for 6 hours. After the reaction, the solvent was removed by using an evaporator, and the residue was added with toluene (10 mL) and hexane (50 mL) to obtain crystals of polyoxyethylene pentaerythritol ether-mono-distearoylphosphadylethanolamine succinate. The crystals were added with ethyl acetate (20 mL), dissolved by warming to 40° C., then added with hexane (20 mL), stirred and then cooled to a temperature below 10° C. to obtain pentaerythritol polyoxyethylene-mono-distearoylphosphadyl-ethanolamine succinate (1.8 g).

Monitoring of the progress of the reaction and identification of the product were performed by thin layer chromatography (TLC) using a silica gel plate. A mixed solvent of chloroform and methanol (volume ratio=85:15) was used as a developing solvent, and the contained substance was quantified by coloration with iodine vapor and comparison with a standard substance of a known amount. The end point of the reaction was confirmed on the basis of the conversion of the spot of polyoxyethylene pentaerythritol ether (average molecular weight: 2000) detected with an Rf value of around 0.6 to 0.7 in TLC described below to a spot detected with an Rf value of around 0.4 to 0.5 due to the binding with the phospholipid compound. The product was confirmed on the basis of the change of the peak of the amino group in phosphatidylethanolamine (3000 $cm^{-1}$) to a peak of carbonyl group (a: 1700 $cm^{-1}$) in the IR spectrum due to conversion of amino group to amide bond, as well as detection of succinate (b) at δ: 2.75 ppm (2H, t), 2.95 ppm (2H, t) by $^1$H-NMR (400 MHz, $CDCl_3$). Further, existence of phospholipid and oxyethylene chain was confirmed by detection of methyl group at the end of the acyl group of distearoylphosphatidylamine at δ: 0.9 ppm (6H, t), methylene group in the acyl group at δ: around 1.25 ppm and polyoxyethylene group at δ: around 3.5 ppm in $^1$H-NMR.

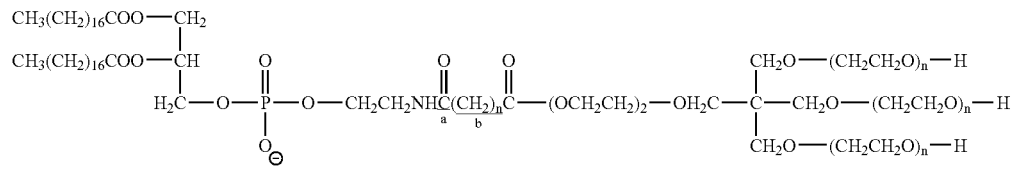

Synthesis Example 2

Synthesis of Polyoxyethylene Diglycerol Ether (Average Molecular Weight: 5000)-mono-distearoylphosphadylethanolamine glutarate

(1) Preparation of Distearoylphosphatidylethanolamine Glutarate

Distearoylphosphatidylethanol (748 mg, 1 mmol) was added with chloroform (50 mL), stirred at 40° C. and further added with triethylamine (100 mg, 1 mmol) to obtain a phospholipid chloroform solution. This solution was added with glutaric anhydride (138.6 mg, 1.05 mmol) and reacted at 40° C. for 2 hours. The end point of the reaction was determined by TLC described below as a point at which distearoylphosphatidylethanol became no longer detectable by ninhydrin coloration. The reaction mixture was cooled and then filtered to remove unreacted distearoylphosphatidylethanolamine, and the filtrate was added with acetone (100 mL) to obtain crystals of distearoylphosphatidylethanolamine glutarate (835 mg).

(2) Synthesis of Polyoxyethylene Diglycerol Ether (Average Molecular Weight: 5000)-mono-distearoylphosphadylethanolamine Glutarate Polyoxyethylene diglycerol ether (average molecular weight: 5000, m=28, 5.25 g, 1.05 mmol) was added with chloroform (40 mL), dissolved in it and warmed to 40° C. to obtain a uniform solution. Then, distearoylphosphatidylethanolamine succinate obtained in the same manner as in Synthesis Example 1 was dissolved in chloroform (10 mL) and added with triethylamine (100 mg, 1 mmol). The reaction and purification were performed in the same manner as in Synthesis Example 1 to obtain polyoxyethylene diglycerol ether-mono-distearoylphosphadylethanolamine succinate (4.0 g).

Monitoring of the progress of the reaction and identification of the product were performed by thin layer chromatography (TLC) in the same manner as in Synthesis Example 1. The end point of the reaction was confirmed by TLC described below on the basis of the conversion of the spot of polyoxyethylene diglycerol ether (average molecular weight: 5000) detected with an Rf value of around 0.6 to 0.7 to a spot detected with an Rf value of around 0.4 to 0.5 due to the binding with the phospholipid compound. The product was confirmed on the basis of the change of the peak of the amino group in the phosphatidylethanolamine (3000 cm$^{-1}$) to a peak of carbonyl group (1700 cm$^{-1}$) in the IR spectrum due to conversion of amino group to amide bond, as well as detection of succinate (—OCOCH$_2$CH$_2$CONH—) at δ: 2.7 ppm (2H, t), 2.9 ppm (2H, t) by $^1$H-NMR (400 MHz, CDCl$_3$). Further, existence of phospholipid and oxyethylene chain was confirmed by detection of methyl group at the end of the acyl group in distearoylphosphatidylamine at δ: 0.9 ppm (6H, t), methylene group in the acyl group at δ: around 1.25 ppm and polyoxyethylene group at δ: around 3.5 ppm by $^1$H-NMR.

Synthesis Example 3

Synthesis of Polyoxyethylens Hexaglycerol Ether (Average Molecular Weight: 2000)-mono-distearoylphosphadylethanolamine succinate Polyoxyethylene hexaglycerol ether (average molecular weight: 2000, m=6, 2.1 g, 1.05 mol) was added with chloroform (20 mL) and dissolved, and then warmed to 40° C. to obtain a uniform solution. Then, distearoylphosphatidylethanolamine succinate obtained in the same manner as in Synthesis Example 1 was dissolved in chloroform (10 mL) and added with triethylamine (100 mg, 1 mmol). In the same manner as in Synthesis Example 1, polyoxyethylene hexaglycerol ether-mono-distearoylphosphadylethanolamine succinate (1.1 g) was obtained.

Monitoring of the progress of the reaction and identification of the product were performed by thin layer chromatography (TLC) in the same manner as in Synthesis Example 1. The end point of the reaction was confirmed by TLC described below on the basis of the conversion of the spot of polyoxyethylene hexaglycerol ether (average molecular weight: 2000) detected with an Rf value of around 0.6 to 0.7 to a spot detected with an Rf value of around 0.4 to 0.5 due to the binding with the phospholipid compound. The product was confirmed on the basis of the change of the peak of the amino group in the phosphatidylethanolamine (3000 cm$^{-1}$) to a peak of carbonyl group (1700 cm$^{-1}$) in the IR spectrum due to conversion of amino group to amide bond, as well as detection of succinate (—OCOCH$_2$CH$_2$CONH—) at δ: 2.7 ppm (2H, t), 2.9 ppm (2H, t) by $^1$H-NMR (400 MHz, CDCl$_3$). Further, existence of phospholipid and oxyethylene chain was confirmed by detection of methyl group at the end of the acyl group in distearoylphosphatidylamine at δ: 0.9 ppm (6H, t), methylene group in the acyl group at δ: around 1.25 ppm and polyoxyethylene group at δ: around 3.5 ppm by $^1$H-NMR.

Synthesis Example 4

Synthesis of Polyoxyethylene Glycerol Ether (Average Molecular Weight: 2000)-mono-distearoylphosphadylethanolamine Succinate Polyoxyethylene glycerol ether (average molecular weight: 2000, m=15, 2.1 g, 1.05 mol) was added with chloroform (20 mL) and dissolved, and then warmed to 40° C. to obtain a uniform solution. Then, distearoylphosphatidylethanolamine succinate obtained in the same manner as in Synthesis Example 1 was dissolved in chloroform (10 mL) and added with triethylamine (100 mg, 1 mmol), and polyoxyethylene glycerol ether-mono-distearoylphosphadylethanolamine succinate (1.9 g) was obtained in the same manner as in Synthesis Example 1.

Monitoring of the progress of the reaction and identification of the product were performed by thin layer chromatography (TLC) in the same manner as in Synthesis Example 1. The end point of the reaction was confirmed by TLC described below on the basis of the conversion of the spot of polyoxyethylene glycerol ether (average molecular weight: 2000) detected with an Rf value of around 0.6 to 0.7 to a spot detected with an Rf value of around 0.4 to 0.5 due to the binding with the phospholipid compound. The product was confirmed on the basis of the change of the peak of the amino group in the phosphatidylethanolamine (3000 cm$^{-1}$) to a peak of carbonyl group (1700 cm$^{-1}$) in the IR spectrum due to conversion of amino group to amide bond, as well as detection of succinate (—OCOCH$_2$CH$_2$CONH—) at δ: 2.7 ppm (2H, t), 2.9 ppm (2H, t) by $^1$H-NMR (400 MHz, CDCl$_3$). Further, existence of phospholipid and oxyethylene chain was confirmed by detection of methyl group at the end of the acyl group in distearoylphosphatidylamine at δ: 0.9 ppm (6H, t), methylene group in the acyl group at δ: around 1.25 ppm and polyoxyethylene group at δ: around 3.5 ppm by $^1$H-NMR.

Synthesis Example 5

Synthesis of Polyoxyethylene Pentaerythritol Ether (Molecular Weight: 5000) glutaryl-mono-distearoylphosphatidylethanolamine (1) Synthesis of Polyoxyethylene Pentaerythritol Ether (Molecular Weight: 5000) Glutarate Polyoxyethylene pentaerythritol ether (molecular weight: 5000, m=28, 5 g, 1 mmol) was added with sodium acetate (3.3 mg, 0.04 mmol) and warmed to 100° C. to obtain a uniform solution. Then, the mixture was added with glutaric anhydride (0.11 g, 1.1 mol) and reacted at 110° C. for 8 hours. The reaction mixture was cooled and then added with isopropyl alcohol (20 mL) to obtain crystals of polyoxyethylene pentaerythritol ether (molecular weight: 5000) glutarate. The crystals were added with chloroform (15 mL), dissolved by warming to 40° C., then added with N-hydroxysuccinimide (0.12 g, 1.1 mmol) and dicyclohexylcarbodiimide (0.43 g, 2.1 mmol), and reacted at 40° C. for 2 hours. After the reaction, the reaction mixture was filtered to obtain a solution of crude polyoxyethylene pentaerythritol ether (molecular weight: 5000) succinimidylglutarate.

(2) Synthesis of Polyoxyethylene Pentaerythritol Ether (Molecular Weight: 5000) glutaryl-mono-distearoylphosphatidylethanolamine Distearoylphosphatidylethanolamine (1.5 g, 2 mmol) was added with chloroform (7 mL) and warmed at 40° C. to obtain a phospholipid chloroform solution. Further, this solution was added with triethylamine (0.2 g, 2 mmol) and stirred at 40° C. This phospholipid solution was slowly added with the aforementioned polyoxyethylene pentaerythritol ether (molecular weight: 5000) succinimidyl glutarate solution and reacted at 40° C. for 5 hours. After the reaction, the solvent was removed by using an evaporator, and the residue was added with toluene (20 mL), dissolved by warming, then added with hexane (40 mL) and stirred to precipitate crystals. These crystals were separated by filtration. The resulting crude crystals were added with ethyl acetate (15 mL), dissolved by warming to 50° C., then added with Kyoward 700 and Kyoward 1000 (0.1 g for each, Kyowa Chemical Industry Co., Ltd.) as adsorbents and stirred for 80 minutes. Kyowards were removed by suction filtration, and the resulting filtrate was added with hexane (10 mL) and cooled to a temperature below 15° C. to precipitate crystals. These crystals were separated by filtration. The resulting crystals were added with ethyl acetate (30 mL) and dissolved by warming to 50° C., and then cooled to a temperature below 15° C. to precipitate crystals. These crystals were collected by filtration. When insoluble solids remained after the dissolution by warming, they were removed by filtration, and then the subsequent step was performed. Further, the resulting crystals were similarly dissolved again in ethyl acetate (20 mL) with warming and added with hexane (10 mL) to precipitate crystals. The precipitated crystals were collected by filtration to obtain crystals with a final purity of 98% (5 g, yield: 94.5%).

The end point of the reaction was confirmed by TLC described below on the basis of the conversion of the spot of polyoxyethylene pentaerythritol ether (average molecular weight: 5000) succinimidyl glutarate detected with an Rf value of around 0.7 to 0.8 to a spot detected with an Rf value of around 0.2 to 0.3 due to the binding with the phospholipid compound. The product was confirmed on the basis of the change of the peak of the amino group in phosphatidylethanolamine (3000 cm$^{-1}$) to a peak of carbonyl group (c: 1700 cm$^{-1}$) in the IR spectrum due to conversion of amino group to amide bond, as well as detection of glutarate (d: —OCOCH$_2$CH$_2$CH$_2$CONH—) at δ: 2.0 ppm (8H, m), 2.5 ppm (8H, t), 2.7 ppm (8H, t) by $^1$H-NMR (400 MHz, CDCl$_3$). Further, existence of phospholipid and oxyethylene chain was confirmed by detection of methyl group at the end of the acyl group in distearoylphosphatidylamine at δ: 0.9 ppm (6H, t), methylene group in the acyl group at δ: around 1.25 ppm and polyoxyethylene group at δ: around 3.5 ppm by $^1$H-NMR.

Further, because the hydroxyl value of polyoxyethylene pentaerythritol ether used as the raw material was 45 mg KOH/g, and the molecular weight of polyoxyethylene pentaerythritol ether (molecular weight: 5000) succinimidylglutarate was found to be 5812 as measured by gel permeation chromatography (GPC), polyoxyethylene having a molecular weight of about 5000 with 4 arms was confirmed. For GPC, SHODEX GPC SYSTEM-11 as a system, SHODEX RI-71 as a differential refractometer and three columns of SHODEX KF804L directly connected were used, and tetrahydrofuran was flowed as a developing solvent at a flow rate of 1 ml/min at a column temperature 40° C. A 0.1% tetrahydrofuran solution (0.1 ml) of the resulting sample was injected. The molecular weight was calculated by using BORWIN GPC Calculation Program.

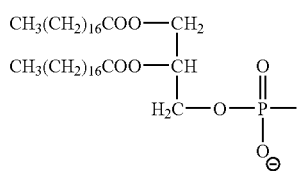
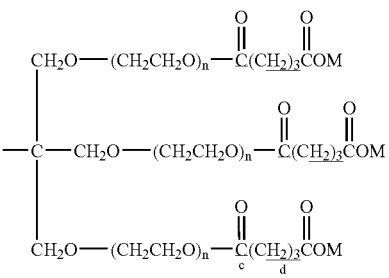

Synthesis Example 6

Synthesis of Polyoxyethylene Hexaglycerin Ether (Molecular Weight: 2000) glutaryl-mono-distearoylphosphatidylethanolamine

(1) Synthesis of Polyoxyethylene Hexaglycerin Ether (Molecular Weight: 2000) glutarate Polyoxyethylene hexaglycerin ether (molecular weight: 2000, m=6, 2 g, 1 mmol) was reacted with glutaric anhydride in the same manner as in Synthesis Example 5 to obtain polyoxyethylene hexaglycerin ether (molecular weight: 2000) glutarate. The reaction product was further reacted with N-hydroxysuccinimide (0.12 g, 1.1 mmol) and dicyclohexylcarbodiimide (0.43 g, 2.1 mmol) to obtain crude polyoxyethylene hexaglycerine ether (molecular weight: 2000) succinimidylglutarate (1.9 g) represented by the following formula (6).

(2) Synthesis of Polyoxyethylene Hexaglycerin Ether (Molecular Weight: 2000) glutaryl-mono-distearoylphosphatidylethanolamine Distearoylphosphatidylethanolamine (1.5 g, 2 mmnol) was reacted with crude polyoxyethylene hexaglycerine ether (molecular weight: 2000) succinimidylglutarate in the same manner as in Synthesis Example 5, and the product was further purified to obtain polyoxyethylene hexaglycerin ether (molecular weight: 2000) glutaryl-mono-distearoylphosphatidylethanolamine (2.2 g).

The end point of the reaction was confirmed by TLC described below on the basis of the conversion of the spot of crude polyoxyethylene hexaglycerine ether (average molecular weight: 2000) succinimidylglutarate detected with an Rf value of around 0.7 to 0.8 to a spot detected with an Rf value of around 0.2 to 0.3 due to the binding with the phospholipid compound. The product was confirmed on the basis of the change of the peak of the amino group in phosphatidylethanolamine (3000 $cm^{-1}$) to a peak of carbonyl group (c: 1700 $cm^{-1}$) in the IR spectrum due to conversion of amino group to amide bond, as well as detection of glutarate (—$OCOCH_2CH_2CH_2CONH$—) at δ: 2.0 ppm (8H, m), 2.5 ppm (8H, t), 2.7 ppm (8H, t) by $^1$H-NMR (400 MHz, $CDCl_3$). Further, existence of phospholipid and oxyethylene chain was confirmed by detection of methyl group at the end of the acyl group in distearoylphosphatidylamine at δ: 0.9 ppm (6H, t), methylene group in the acyl group at δ: around 1.25 ppm and polyoxyethylene group at δ: around 3.5 ppm by $^1$H-NMR. Further, because the hydroxyl value of polyoxyethylene hexaglycerin ether used as the raw material was 221 mg KOH/g, polyoxyethylene having a molecular weight of about 2000 with 8 branches was confirmed.

Synthesis Example 7

Synthesis of Polyoxyethylene Pentaerythritol Ether (Molecular Weight: 2000) succinyl-mono-distearoylphosphatidylethanolamine

(1) Synthesis of Polyoxyethylene Pentaerythritol Ether (Molecular Weight: 2000) Succinate Polyoxyethylene pentaerythritol ether (molecular weight: 2000, m=11, 2 g, 1 mmol) was added with sodium acetate (3.3 mg, 0.04 mmol) and warmed to 100° C. to obtain a uniform solution, then added with succinic anhydride (0.11 g, 1.1 mol) and reacted at 110° C. for 5 hours. The reaction mixture was cooled and then added with isopropyl alcohol (20 mL) to obtain crystals of polyoxyethylene pentaerythritol ether (molecular weight: 2000) succinate. These crystals were added with chloroform (15 mL) and dissolved by warming to 40° C., then added with N-hydroxysuccinimide (0.12 g. 1.1 mmol) and dicyclohexylcarbodiimide (0.43 g, 2.1 mmol) and reacted at 40° C. for 2 hours. After the reaction, the reaction mixture was filtered to obtain a solution of crude polyoxyethylene pentaerythritol ether (molecular weight: 2000) succinimidylsuccinate.

(2) Synthesis of Polyoxyethylene Pentaerythritol Ether (Molecular Weight: 2000) succinyl-mono-distearoylphosphatidylethanolamine Distearoylphosphatidylethanolamine (1.5 g, 2 mmol) was added with chloroform (7 mL) and heated to 40° C. to obtain a phospholipid chloroform solution. Further, the solution was added with triethylamine (0.2 g, 2 mmol) and stirred at 40° C. This phospholipid solution was slowly added with the aforementioned solution of crude polyoxyethylene pentaerythritol ether (molecular weight: 2000) succinimidylsuccinate and reacted at 40° C. for 5 hours. After the reaction, the solvent was removed by using an evaporator, and the residue was added with toluene (20 mL) and dissolved by warming, then added with hexane (40 mL) and stirred to precipitate crystals. These crystals were separated by filtration. The resulting crude crystals were dissolved in ethyl acetate (15 mL) with warming at 50° C., added with Kyoward 700 and Kyoward 1000 (0.1 g for each) as adsorbents and stirred for 30 minutes. Kyowards were removed by suction filtration, and the resulting filtrate was added with hexane (10 mL) and cooled to a temperature below 15° C. to precipitate crystals. These crystals were separated by filtration. The resulting crystals were added with ethyl acetate (30 mL), dissolved by warming to 50° C. and then cooled to a temperature below 15° C. to precipitate crystals. These crystals were collected by filtration. When insoluble solids remained after the dissolution by warming, they were removed by filtration, and then the subsequent step was performed. Further, the resulting crystals were similarly dissolved again in ethyl acetate (20 mL) with warming and added with hexane (10 mL) to precipitate crystals. The precipitated crystals were collected by filtration to obtain crystals (5 g) with a final purity of 98% (yield: 94.5%).

The end point of the reaction was confirmed by TLC described below on the basis of the conversion of the spot of crude polyoxyethylene pentaerythritol ether (average molecular weight: 2000) succinimidylsuccinate detected with an Rf value of around 0.7 to 0.8 to a spot detected with an Rf value of around 0.2 to 0.3 due to the binding with the phospholipid compound. The product was confirmed on the basis of the change of the peak of the amino group in phosphatidylethanolamine (3000 $cm^{-1}$) to a peak of carbonyl group (c: 1700 $cm^{-1}$) in the IR spectrum due to conversion of amino group to amide bond, as well as detection of succinate (b) at δ: 2.75 ppm (2H, t), 2.95 ppm (2H, t) by $^1$H-NMR (400 MHz, $CDCl_3$). Further, existence of phospholipid and oxyethylene chain was confirmed by detection of methyl group at the end of the acyl group in distearoylphosphatidylamine at δ: 0.9 ppm (6H, t), methylene group in the acyl group at δ: around 1.25 ppm and polyoxyethylene group at δ: around 3.5 ppm by $^1$H-NMR.

Further, because the hydroxyl value of polyoxyethylene pentaerythritol ether used as the raw material was 26.7 mg KOH/g, and the molecular weight of polyoxyethylene pentaerythritol ether (molecular weight: 2000) succinimidylsuccinate was found to be 2082 as measured by gel permeation chromatography (GPC), polyoxyethylene having a molecular weight of about 2000 with 4 branches was confirmed. For GPC, SHODEX GPC SYSTEM-11 as a system, SHODEX RI-71 as a differential refractometer and three columns of SHODEX KF804L directly connected were used, and tetrahydrofuran was flowed as a developing solvent at a flow rate of 1 ml/min at a column temperature 40° C. A 0.1 weight % tetrahydrofuran solution (0.1 ml) of the resulting sample was injected. The molecular weight was calculated by using BORWIN GPC Calculation Program.

Example 1

Preparation of Lotion (Evaluation as Solubilizer)

Lotion was prepared by using polyoxyethylene pentaerythritol ether (molecular weight: 5000) glutaryl-mono-distearoylphosphatidylethanolamine obtained in Synthesis Example 5. Among the base materials in the composition shown in Table 1, glycerin and propylene glycol were added to purified water and uniformly dissolved. The other base materials were added to ethanol to obtain a uniform solution, and then added to the aforementioned purified aqueous phase with stirring and solubilized to obtain lotion.

Composition example:

| | |
|---|---|
| Propylene glycol | 5.0% by weight |
| Glycerin | 2.0% by weight |
| Oleyl alcohol | 0.5% by weight |
| Hydrogenated soybean lecithin | 0.5% by weight |
| Ethanol | 7.0% by weight |
| Polyoxyethylene pentaerythritol ether (molecular weight: 5000) glutaryl-mono-distearoylphoaphatidylethanolamine | 2.0% by weight |
| Tocopherol | 0.02% by weight |
| Fragrant | Suitable amount |
| Preservative | Suitable amount |
| Purified water | 73.0% by weight |

Example 2

Preparation of Milky Lotion (Evaluation as Dispersing Agent for Cosmetics)

Preparation Method of Liposomes

Hydrogenated soybean phosphatidylcholine (645 mg), cholesterol (299 mg) and myristic acid (23 mg) (molar ratio: 1:1:0.1) were added with polyoxyethylene pentaerythritol ether (molecular weight: 5000) glutarate at a mixed lipid concentration of 5 mole %, added with physiological saline (10 to 11 mL) warmed to 60° C. beforehand at a mixed lipid concentration of 10% by weight, stirred and further blended in a homogenizer on a water bath at 60° C. for 10 minutes to obtain a liposome solution.

Among the base materials in the composition shown in Table 2, those of the oil phase including an emulsifier were uniformly dissolved by using the above liposome solution with warming at 60° C. to form a uniform solution, and added with the aqueous phase with stirring at the same temperature to obtain a milky lotion.

| | |
|---|---|
| Oil phase: | |
| Cetanol | 2.0% by weight |
| Vaseline | 2.0% by weight |
| Squalane | 5.0% by weight |
| Liquid paraffin | 10.0% by weight |
| Polyoxyethylene monooleate | 2.0% by weight |
| Tocopherol | 0.02% by weight |
| Fragrant | Suitable amount |
| Preservative | Suitable amount |
| Aqueous phase: | |
| Propylene glycol | 2.0% by weight |
| Purified water | 87.0% by weight |
| Liposome solution | 10.0% by weight |

Comparative Synthesis Example 1

(1) Synthesis of monomethylpolyoxyethylenecarbamyl (Molecular Weight: 2000) distearoylphosphatidylethanolamine Monomethoxypolyoxyethylene (molecular weight: 2000, 20 g, 10 mmol) was added with toluene (80 mL), heated to 110° C. and refluxed for dehydration. The residue was added with 1,1'-carbonyldiimidazole (1.95 g, 12 mmol) and reacted at 40° C. for 2 hours. The reaction mixture was added with pyridine (1.58 g, 20 mmol) and distearoylphosphatidylethanolamine (7 g, 9.36 mmol) and reacted at 65° C. for 5 hours. The reaction mixture was added with hexane (300 mL) and crystallized. The crystals were added with ethyl acetate (400 mL), dissolved at 65° C., stirred for 30 minutes, and then cooled to 5° C. The precipitated crystals were collected by filtration. In the same manner, the step using ethyl acetate was performed once.

The crystals were dissolved in ethyl acetate (400 mL), added with Kyoward 700 (1 g) as an adsorbent and stirred at 65° C. for one hour. The reaction mixture was filtered and then cooled to 5° C. for crystallization. The crystals were washed with hexane (200 mL), collected by filtration and dried to obtain monomethylpolyoxy-ethylenecarbamyl (molecular weight: 2000) distearoylphosphatidylethanolamine (15.3 g) with a purity of 98.3% (yield: 54.7%).

The product was analyzed by thin layer chromatography (TLC) using a silica gel plate. A mixed solvent of chloroform and methanol with a mixing ratio of 85:15 (weight ratio) was used as a developing solvent, and identification and quantification of the contained substance were performed by coloration with iodine vapor and comparison with a standard substance of a known amount.

Example 3

Determination of Salt Tolerant Effect (Evaluation as Surfactant)

Clouding point of the polyoxyethylene pentaerythritol ether (average molecular weight: 2000)-mono-distearoylphosphadylethanolamine obtained in Synthesis Example 1 was measured for a 1 weight % solution in 5 weight % aqueous sodium sulfate. As a result of the measurement, the clouding point was not detectable even when the temperature was raised up to 80° C.

Comparative Example 1

Comparison of Salt Tolerant Effect (Evaluation as Surfactant)

Clouding point of the monomethylpolyoxyethylenecarbamyl (molecular weight: 2000) distearoylphosphatidylethanolamine obtained in Comparative Synthesis Example 1 was measured in the same manner as in Example 3. As a result of the measurement, the clouding point was found to be 50.0° C.

This result showed that a branched polyoxyethylene phospholipid derivative exhibited high salt tolerance.

Example 4

Evaluation as Long Circulating Liposomes (1) Preparation of Liposomes

Lipids in the membrane composition ratios shown in Table 1 (Formulation Examples 1 to 4, Control Examples 1 and 2) were weighed and dissolved in a mixture of chloroform and methanol (2:1). Then, the organic solvent was evaporated by using an evaporator, and the residue was further dried for one hour under reduced pressure. Then, this dried lipid product (lipid film) was added with 155 mM aqueous ammonium sulfate (pH 5.5, 10 ml) warmed to 65° C. beforehand and gently stirred by using a vortex mixer on a warm water bath (until lipids were substantially exfoliated from an eggplant-shaped flask). This lipid dispersion was transferred to a homogenizer and homogenized for 10 strokes, and then the sizing procedure was performed by using polycarbonate membrane filters with various pore sizes (0.2 μm×3 times, 0.1 μm×3 times, 0.05 μm×3 times and 0.03 μm×3 times) to prepare an empty liposome dispersion having a particle diameter of about 100 nm.

This empty liposome dispersion (4 ml) was diluted 2.5 times with physiological saline. This diluted liposome dispersion was put into a ultracentrifugation tube, centrifuged at 65000 rpm for one hour, and then the supernatant was discarded. The residue was resuspended in physiological saline in the volume of the liposome dispersion before the centrifugation (10 ml, the total lipid concentration was adjusted to 50 mM at this point). The aforementioned empty liposome dispersion (total lipid concentration: 50 mM) of which external aqueous phase was replaced with physiological saline and a doxorubicin solution (medicament concentration: 3.3 mg/ml of physiological saline) were warmed to 60° C. beforehand, and 4 parts by volume of the empty liposome dispersion was added with 6 parts by volume of the doxorubicin solution (that is, the final medicament concentration was 2.0 mg/ml, and the final lipid concentration was 20 mM) and incubated at 60° C. for one hour. Then, the mixture was cooled to room temperature to obtain a doxorubicin-containing liposome dispersion.

(2) Physicochemical Properties of Liposomes

The encapsulation efficiency of doxorubicin in the liposomes was obtained by subjecting a part of the aforementioned liposome dispersion to gel filtration (Sephadex G-50, the mobile phase consisted of physiological saline) and quantifying doxorubicin in the liposome fraction eluted in the void volume using liquid chromatography. Further, the particle diameter was measured by the quasi-elastic light scattering (QELS) method using a part of the aforementioned liposome dispersion, As a result, the encapsulation efficiency of the active ingredient, doxorubicin, in the liposomes was 100% except for Formulation Example 4 as shown in Table 1. Therefore, each original liposome dispersion was used as it was, and diluted 4/3 times with physiological saline for the experiment for blood retention property in rats described below (the final medicament concentration was 1.5 mg/ml, and the final lipid concentration was 15 mM). Further, the liposomes of Formulation Example 4 were subjected to ultracentrifugation (65,000 rpm, one hour) to remove the unencapsulated medicament in the supernatant and adjusted to a final medicament concentration of 1.5 mg/ml with physiological saline (the final lipid concentration was about 20.0 mM). The particle diameter was about 100 nm for all of the liposomes.

(3) Experiment for Blood Retention Property in Rats

An experiment for examining blood retention property was performed in SD male rats (6-week old) by using the liposome dispersions of Formulation Examples 1 to 4 and Control Examples 1 and 2. Each liposome dispersion was administered from the cervical veins of rats under etherization (each group consisted of 5 rats, the dose was 7.5 mg doxorubicin/5 ml/kg). Then, heparinized blood (0.5 to 1 ml) was collected from the cervical veins under etherization at each of blood collection time points (2, 4, 8, 24, 48, 72, 120, 168 hours), and plasma was separated. Then, each sample was pretreated by a conventional method, and plasma concentration of the medicament was measured by HPLC. The AUC (0-∞) was obtained from the concentration of the medicament in plasma in each liposome dispersion formulation according to the trapezoidal rule. As shown in Table 1, in comparison with the AUCs of the liposomes of Control Example 1, which did not contain the lipid derivative of the present invention, or the liposomes of Control Example 2, which contained only ea phospholipid portion of the lipid derivative of the present invention (DSPE: distearoylphosphatidylethanolamine), the liposome formulations containing the lipid derivatives of the present invention (Formulation Examples 1 to 4) achieved AUCs greater by one or more orders, and thus showed evident blood retention property.

TABLE 1

| | Liposome membrane composition | Particle diameter (nm) | Retention ratio of active ingredient (%) | $AUC_{0-\infty}$ ± S.D. (μg · hr/mL) |
|---|---|---|---|---|
| Formulation Example 1 | DSPE-GLY20H/HSPC/Cholesterol = 1.04 mM/11.28 mM/7.68 mM *DSPE-GLY20H: Synthesized in Synthesis Example 4 HSPC: Hydrogenated soybean phosphatidylcholine | 88 | 100.0 | 3185 ± 662 |
| Formulation Example 2 | DSPE-PTE20H/HSPC/Cholesterol = 1.04 mM/11.28 mM/7.68 mM *DSPE-PTE20H: Synthesized in Synthesis Example 1 HSPC: Hydrogenated soybean phosphatidylcholine | 108 | 100.0 | 6584 ± 739 |
| Formulation Example 3 | DSPE-HGEO20H/HSPC/Cholesterol = 1.04 mM/11.28 mM/7.68 mM *DSPE-HGEO20H: Synthesized in Synthesis Example 3 HSPC: Hydrogenated soybean phosphatidylcholine | 101 | 100.0 | 6028 ± 689 |

TABLE 1-continued

| | Liposome membrane composition | Particle diameter (nm) | Retention ratio of active ingredient (%) | $AUC_{0-\infty} \pm S.D.$ (μg · hr/mL) |
|---|---|---|---|---|
| Formulation Example 4 | DSPE-PTESA20H/HSPC/Cholesterol = 1.04 mM/11.28 mM/7.68 mM *DSPE-PTESA20H: synthesized in Synthesis Example 7 HSPC: Hydrogenated soybean phosphatidylcholine | 68 | 74.8 | 4300 ± 494 |
| Control Example 1 | HSPC/Cholesterol = 11.90 mM/8.10 mM *HSPC: Hydrogenated soybean phosphatidylcholine | 91 | 100.0 | 452 ± 98 |
| Control Example 2 | DSPE/HSPC/Cholesterol = 1.04 mM/11.28 mM/7.68 mM *DSPE: Distearoylphosphatidylcholine HSPC: Hydrogenated soybean phosphatidylcholine | 94 | 100.0 | 397 ± 133 |

INDUSTRIAL APPLICABILITY

The phospholipid derivatives of the present invention are highly safe for living bodies, and are useful as surfactants, solubilizers, or dispersing agents in the field of cosmetics and the like. When the phospholipid derivatives of the present invention, which are polyoxyethylene derivatives having multi-arm, are used for manufacture of lipid membrane structures such as liposomes, the lipid membrane structures are not instabilized, the aggregation of microparticles in an aqueous medium is prevented, and thus a stable state of a solution can be obtained. Furthermore, liposomes containing the phospholipid derivatives of the present invention are characterized by superior blood retention property.

What is claimed is:

1. A phospholipid derivative represented by the following general formula (1):

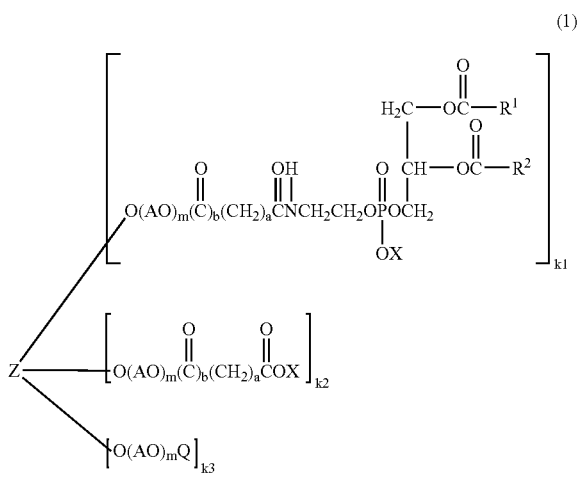

wherein Z represents a residue of a compound having 3 to 10 hydroxyl groups; AO represents an oxyalkylene group having 2 to 4 carbon atoms; $R^1CO$ and $R^2CO$ independently represent an acyl group having 8 to 22 carbon atoms; X represents hydrogen atom, an alkali metal atom, ammonium or an organic ammonium; "a" represents an integer of 0 to 4; "b" represents 0 or 1; Q represents hydrogen atom or methyl group; m represents an average number of moles of the oxyalkylene group added; and m, k1, k2, and k3 are numbers satisfying the following conditions: $3 \leq m \leq 200$, $9 \leq m \times (k1+k2+k3) \leq 1000$, $1 \leq k1 \leq 2$, $0 \leq k2 \leq 9$ and $0 \leq k3 \leq 9$, and $3 \leq k1+k2+k3 \leq 10$.

2. The phospholipid derivative according to claim 1, wherein the condition $4 \leq k1+k2+k3 \leq 8$ is satisfied.

3. The phospholipid derivative according to claim 1, wherein $R^1CO$ and $R^2CO$ independently represent an acyl group having 12 to 20 carbon atoms.

4. The phospholipid derivative according to claim 1, wherein k2 is 0.

5. The phospholipid derivative according to claim 4, wherein "a" and "b" represent 0.

6. The phospholipid derivative according to claim 1, wherein the following conditions k3<1 and k2>k3 are satisfied.

7. A surfactant containing the phospholipid derivative according to claim 1.

8. A lipid membrane structure containing the phospholipid derivative according to claim 1.

9. A liposome containing the phospholipid derivative according to claim 1.

10. A method for producing the phospholipid derivative according to claim 1, which comprises the step of reacting a phospholipid compound represented by the following general formula (2):

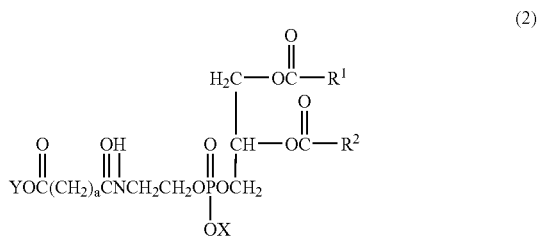

wherein $R^1CO$ and $R^2CO$ independently represent an acyl group having 8 to 22 carbon atoms; X represents hydrogen atom, an alkali metal atom, ammonium or an organic ammonium; "a" represents an integer of 0 to 4; and Y represents hydrogen atom or N-hydroxysuccinimide, with a polyalkylene oxide compound represented by the following general formula (3)

wherein Z represents a residue of a compound having 3 to 10 hydroxyl groups; AO represents one or two or more kinds of oxyalkylene groups having 2 to 4 carbon atoms, and when AO represents two or more kinds of oxyalkylene groups, they may bond to form a block or random copolymer; m represents an average number of moles of the oxyalkylene group added;

and m and k are numbers satisfying the following conditions: $3 \leq m \leq 200$, $9 \leq m \times k \leq 1000$, and $3 \leq k \leq 10$, in organic solvents in the presence of a basic catalyst.

11. A method for producing the phospholipid derivative according to claim 1, which comprises the step of reacting a polyalkylene oxide derivative represented by the following general formula (4):

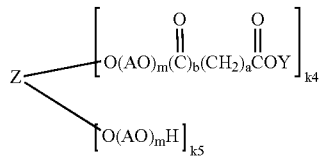

(4)

wherein Z represents a residue of a compound having 3 to 10 hydroxyl groups, "a" represents an integer of 0 to 4; "b" represents 0 or 1; m represents an average number of moles of the oxyalkylene group added; Y represents hydrogen atom or N-hydroxysuccinimide; and k4 and k5 are numbers satisfying the following conditions:

$1 \leq k4 \leq 10$, $0 \leq k5 \leq 9$, and $3 \leq k4+k5 \leq 10$, with a phospholipid derivative represented by the following general formula (5)

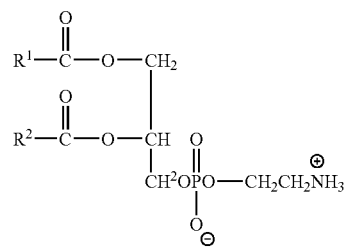

(5)

wherein $R^1CO$ and $R^2CO$ have the same meanings as defined in the aforementioned formula (1), in an organi solvent in the presence of a basic catalyst.

12. A pharmaceutical composition containing the lipid membrane structure according to claim 8 and a medicament.

13. The pharmaceutical composition according to claim 12, wherein the medicament is an antitumor agent.

* * * * *